United States Patent [19]

Hall et al.

[11] 4,011,337
[45] Mar. 8, 1977

[54] OXAMIDE-OXAMIC COMPOUNDS, COMPOSITIONS AND METHODS OF USE

[75] Inventors: Charles M. Hall; Richard S. P. Hsi; John B. Wright, all of Kalamazoo, Mich.

[73] Assignee: The Upjohn Company, Kalamazoo, Mich.

[22] Filed: July 7, 1975

[21] Appl. No.: 593,632

[52] U.S. Cl. .......................... 424/309; 260/268 R; 260/268 CN; 260/465 D; 260/471 A; 260/501.1; 260/501.17; 260/518 A; 260/518 R; 260/519; 260/558 A; 260/559 A; 424/250; 424/304; 424/316; 424/317; 424/324

[51] Int. Cl.[2] ................ A61K 31/24; C07C 103/28

[58] Field of Search ....... 260/471 A, 518 R, 518 A, 260/519; 424/309, 316, 317

[56] References Cited

FOREIGN PATENTS OR APPLICATIONS

| | | |
|---|---|---|
| 812,743 | 3/1974 | Belgium |
| 2,362,409 | 6/1974 | Germany |

*Primary Examiner*—Dolph H. Torrence
*Attorney, Agent, or Firm*—Martin B. Barancik; Roman Saliwanchik

[57] ABSTRACT

Compounds of the formula below are useful in the prophylactic treatment of sensitized humans and animals for allergy and anaphylactic reactions of a reagin or non-reagin mediated nature. The compounds are formulated with pharmaceutical carriers for administration.

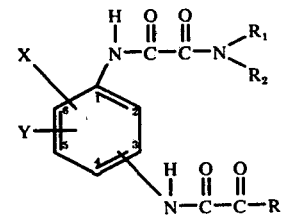

12 Claims, No Drawings

OXAMIDE-OXAMIC COMPOUNDS, COMPOSITIONS AND METHODS OF USE

BRIEF SUMMARY OF THE INVENTION

It has now been discovered that novel compounds of FIG. I are useful in the prophylactic treatment of sensitized humans and animals for allergy and anaphylactic reactions of a reagin or non-reagin mediated nature. The compounds are formulated with pharmaceutical carriers for oral, parenteral, inhalation or rectal means of administration.

DETAILED DESCRIPTION OF THE INVENTION

In accordance with this invention, there are provided compounds represented by FIG. I and hereafter referred to as Group A

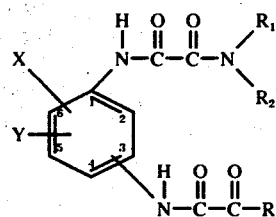

Figure I wherein X and Y are the same or different and are selected from the group consisting of hydrogen, fluorine, chlorine, bromine, trifluoromethyl, cyano, carboxy, carboxyamide, acetyl, phenyl, alkyl of one to six carbon atoms, inclusive, alkoxy of one to six carbon atoms, inclusive, and nitro;

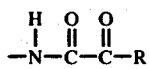

is at the 3 or 4 position;

$R_1$ and $R_2$ are the same or different and are selected from the group consisting of hydrogen, alkyl of one to six carbon atoms, inclusive, monohydroxyalkyl wherein alkyl is from two to six carbon atoms, inclusive, and the hydroxy is not on the alpha carbon atom, and tris(hydroxymethyl)methyl with the proviso that when $R_1$ has a tertiary carbon atom adjacent to the nitrogen atom, $R_2$ does not have a tertiary carbon atom adjacent to the nitrogen atom, R is selected from the group consisting of

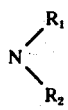

and

OM wherein M is selected from the group consisting of hydrogen, a physiologically acceptable metal or amine cation, and alkyl of one to six carbon atoms, inclusive.

A further group of compounds of FIG. I are compounds wherein X and Y are the same or different and are selected from the group consisting of hydrogen, fluorine, chlorine, trifluoromethyl, cyano, carboxy, acetyl, phenyl, alkyl of one to four carbon atoms, inclusive, alkoxy of one to four carbon atoms, inclusive, and nitro;

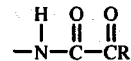

is at the 3 or 4 position, $R_1$ and $R_2$ are the same or different and are selected from the group consisting of hydrogen, alkyl of one to four carbon atoms, inclusive, monohydroxyalkyl wherein alkyl is from two to four carbon atoms, inclusive, and the hydroxy is not on the alpha carbon atom, and tris(hydroxymethyl)methyl with the proviso that when $R_1$ has a tertiary carbon atom adjacent to the nitrogen atom, $R_2$ does not have a tertiary carbon atom adjacent to the nitrogen atom, R is selected from the group consisting of

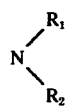

and OM wherein M is selected from the group consisting of hydrogen, a physiologically acceptable metal or amine cation and alkyl of one to four carbon atoms, inclusive.

Another group of compounds of FIG. I are compounds wherein X and Y are the same or different and are selected from the group consisting of hydrogen, fluorine, chlorine, trifluoromethyl, cyano, acetyl, phenyl, alkyl of one to three carbon atoms, inclusive, alkoxy of one to three carbon atoms, inclusive, and nitro,

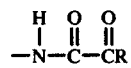

is at the 3 position, $R_1$ and $R_2$ are the same or different and are selected from the group consisting of hydrogen, alkyl of one to three carbon atoms, inclusive, monohydroxyalkyl wherein alkyl is two or three carbon atoms, inclusive, and hydroxy is not on the alpha carbon atom, R is selected from the group consisting of

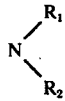

and OM wherein M is selected from the group consisting of hydrogen, a physiologically acceptable metal or amine cation and alkyl of one to three carbon atoms, inclusive.

A still further group of compounds of FIG. I are compounds wherein X and Y are the same or different, are located at the 2 and 5 positions and are selected from the group consisting of hydrogen, fluorine, chlorine, trifluoromethyl, cyano, alkyl of one to three carbon atoms, inclusive, and alkoxy of one to three carbon atoms, inclusive,

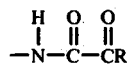

is at the 3 position,
R₁ and R₂ are defined as immediately above,
R is selected from the group consisting of

and OM wherein M is selected from the group consisting of hydrogen and a physiologically acceptable metal or amine cation.

Another group of compounds are those of the immediately above subgroup wherein R is

Another group of compounds are those of the immediately above subgroup wherein R is OM.

The most preferred compound is ethyl 3'-(N²-propyloxamido)oxanilate.

As employed in the above disclosure and throughout the specification, the term "halogen" includes fluoro, chloro, bromo and iodo. The term "alkyl" includes methyl, ethyl, propyl, and isopropyl when limited to three carbon atoms, and additionally includes n-butyl, n-pentyl, n-hexyl and isomers thereof when limited to six carbon atoms. The term "physiologically acceptable metal" includes alkali metals such as sodium and potassium, alkaline earth metals such as calcium and magnesium and other acceptable metals such as aluminum. The term "amine cation" includes all pharmaceutically acceptable cations from amines such as ammonia, tris(hydroxymethyl)aminomethane, D-threo-2-amino-1-p-nitrophenyl-1,3-propanediol, N,N-bis(hydroxyethyl)-piperazine, 2-amino-2-methyl-1-propanol, 2-amino-2-methyl-1,3-propanediol and 2,2-bis(hydroxymethyl)-2,2',2''-nitrilotriethanol and further amines including H₂NR', HNR'₂ and NR'₃, wherein R' is selected from the group consisting of alkyl from one to three carbon atoms, inclusive, and —CH₂CH₂OH.

The compounds of this invention can be prepared by methods known to the art. For example, the diamides, that is compounds of the invention where R is

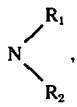

are readily prepared by reacting the analogous diester with the

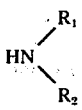

amine in an organic solvent which solubilizes the diester and which is substantially inert to the reactants. Generally a molar ratio of at least two to one amine to diester is used.

The monoamide, that is, compounds of the invention where R is OM, are prepared by reacting the analogous diester with a single mole of the desired amine

in an organic solvent which solubilizes the diester and which is substantially inert to the reactants. The monoamide is isolated from the reaction mass by conventional procedures such as chromatography. An additional procedure for preparing the monoamide is starting with the appropriately substituted nitroaniline, building an oxamate ester at the amino group by standard means, converting the ester to the amide by the above means, reducing the nitro to the amino and then proceeding to the appropriate M grouping by the above means.

The starting material diesters are readily prepared by the procedures of Belgian Pat. No. 808,898, page 7, line 17 to page 8, line 4, and page 9, line 14 to page 10, line 11.

Appropriate solvents which can be used in the conversion of the ester groups to the amide are readily known to those skilled in the art. For example, lower alcohols of one to three carbon atoms, halogenated hydrocarbons of one to three carbon atoms, sulfoxides and formamides. Illustrative examples of these classes of solvents are methanol, ethanol, propanol, isopropanol, chloroform, methylene chloride, ethylene dichloride, dimethylsulfoxide and dimethylformamide.

Following is an illustrative list of compounds of the invention which can be prepared by the above disclosed procedures.

TABLE I

R is N(R₁)(R₂)

| R₁ | R₂ | X | Y |
|---|---|---|---|
| H | H | H | H |
| H | CH₃ | 2-CH₃ | H |
| H | iC₃H₇ | 2-iC₃H₇ | H |
| H | C₅H₁₁ | 2-C₅H₁₁ | H |
| C₂H₅ | C₆H₁₃ | 2-C₆H₁₃ | H |
| C₃H₇ | C₃H₇ | 2-Br | H |
| H | C₂H₄OH | 2-F | H |
| CH₃ | C₃H₆OH | 2-CN | H |
| C₄H₉ | C₂H₃(OH)C₂H₅ | 2-CONH₂ | H |
| C₃H₆OH | C₃H₆OH | 2-CF₃ | H |
| H | C(CH₂OH)₃ | 2-COCH₃ | H |
| C₂H₅ | C(CH₂OH)₃ | 2-NO₂ | H |
| C₅H₁₀OH | C(CH₂OH)₃ | 2-COOH | H |
| C₆H₁₀OH | C(CH₂OH)₃ | 2-C₆H₅ | H |
| H | H | 2-O—iC₃H₇ | H |
| H | C₂H₅ | 2-O—C₄H₉ | H |
| H | i-C₄H₉ | 2-O—iC₆H₁₃ | H |

The above molecule is singly substituted with each of the above X substituents at the 4 position or at the 5-position.

| R₁ | R₂ | X | Y |
|---|---|---|---|
| C₂H₅ | C₂H₅ | 2—Cl | 5—CN |
| H | C₃H₆OH | 2—CH₃ | 5—COOH |
| C₂H₅ | C₃H₅(OH)CH₃ | 2—OC₅H₁₁ | 5—CONH₂ |
| t-C₄H₉ | C₃H₅(OH)C₂H₅ | 2—COCH₃ | 5—CF₃ |
| C₂H₄OH | C₂H₄OH | 2—C₆H₅ | 5—Cl |
| H | C(CH₂OH)₃ | 2—C₂H₅ | 5—NO₂ |
| C₃H₇ | C(CH₂OH)₃ | 2—F | 5—CN |
| C₂H₄OH | C(CH₂OH)₃ | 2—CH₃ | 5—CN |
| H | H | 2—Br | 4—C₂H₅ |
| H | C₆H₁₃ | 2—CF₃ | 4—OC₄H₉ |
| i-C₃H₇ | i-C₃H₇ | 2—COOH | 4—C₆H₅ |
| C₂H₅ | C₄H₉ | 2—NO₂ | 4—CONH₂ |
| H | C₄H₈OH | 2—C₂H₅ | 4—C₂H₅ |
| C₃H₆OH | C₃H₆OH | 2—OC₃H₇ | 4—OC₃H₇ |
| C₂H₄(OH)C₃H₇ | C(CH₂OH)₃ | 2—COOH | 4—COOH |
| H | C(CH₂OH)₃ | 2—Cl | 4—Cl |
| CH₃ | C(CH₂OH)₃ | C₆H₅ | 4—CH₃ |
| C₂H₅OH | C(CH₂OH)₃ | 2—Cl | 5—C₆H₅ |
| H | H | 2—NO₂ | 5—NO₂ |
| C₂H₅ | C₂H₅ | 2—Br | 5—Br |
| C₄H₉ | C₄H₉ | 2—CONH₂ | 5—CONH₂ |

TABLE II

Each of the X and Y substituted compounds of Table I are prepared where R is OM and M is any of the following substituents.

| M |
|---|
| H |
| CH₃ |
| C₂H₅ |
| C₃H₇ |
| i-C₃H₇ |
| C₄H₉ |
| t-C₄H₉ |
| C₅H₁₁ |
| iC₆H₁₃ |
| Na |
| K |
| Li |
| Al |
| Ca |
| Mg |
| NH₄ |
| N(CH₂CH₃)₃ |
| N(CH₂OH)₃ |

TABLE III

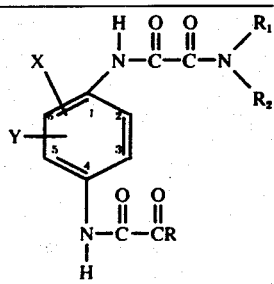

Each of the X, Y, R₁ and R₂ substituted compounds of Tables I and II are prepared wherein the second oxamic group is at position 4 as shown in this table. In so doing, it should be noted that the 2,4-disubstituted compounds of Table II are now denominated 2,3-disubstituted molecules. Furthermore, each one of these is repeated at the 2,6 positions. This change and addition in numbering is due to the position of the second oxamic group at the 4 position rather than the 3 position.

Tables II and III are not rendered in the same manner as Table I for the purpose of brevity. However, the same scoping as Table I is intended.

The following examples are compounds in accordance with this invention. The compounds are intended not to limit but merely to exemplify the nature of the invention. All temperatures are in Centigrade.

EXAMPLE 1

N',N''-[2-chloro-5-cyano-m-phenylene]-bis-[N'-(2-hydroxy-1,1-bis(hydroxymethyl)ethyl]oxamide A mixture of 368 mg. (0.001 mole) of diethyl N,N'-(2-chloro-5-cyano-m-phenylene)dioxamate and 25 ml. of 0.08 M solution of tris(hydroxymethyl)aminomethane (THAM) in methanol (0.002 mole) is heated under reflux under a nitrogen atmosphere for one hour and then stirred overnight at room temperature. The mixture is filtered and the precipitate washed with methanol. There is obtained 317 mg. (61.3%) of material melting at 203°–204° (dec.).

Analysis: Calc'd. for $C_{19}H_{24}ClN_5O_{10}$ C, 44.06; H, 4.67; Cl, 6.85; N, 13.52. Found: C, 43.75; H, 4.76; Cl, 6.84; N, 13.33.

EXAMPLE 2

N,N'-2-chloro-5-(trifluoromethyl)-m-phenylene-bis[N'-(2-hydroxy-1,1-bis(hydroxymethyl)ethyl]oxamide A mixture of 4.11 gm. (0.01 mole) of diethyl N,N'-[2-chloro-5-(trifluoromethyl)-m-phenylene]dioxamate, 2.42 gm. (0.02 mole) of THAM and 75 ml. of absolute ethanol is refluxed for three hours. The mixture is cooled to room temperature. There is added 37 ml. of water and refluxing is continued for three hours. The solution is cooled to room temperature and the solution refrigerated. The colorless needles are removed by filtration. There is obtained 2.30 gm. (41%) that melts at 258° (dec.).

Analysis: Calc'd. for $C_{19}H_{24}ClF_3N_4O_{10} \cdot H_2O$ C, 39.42; H, 4.53; Cl, 6.13; F, 9.85; N, 9.68. Found: C, 39.92; H, 4.25; Cl, 6.41; F, 10.06; N, 9.72.

EXAMPLE 3

Ethyl 2'-chloro-5'-cyano-3'-[$N^2$-[2-hydroxy-1,1-bis(hydroxymethyl)ethyl]oxamido]oxanilate To a solution of 0.600 gm. (0.005 mole) of tris(hydroxymethyl)aminomethane in 50 ml. of absolute ethanol is added 1.839 mg. (0.005 mole) of diethyl N,N'-(2-chloro-5-cyano-m-phenylene)dioxamate in 50 ml. of methylene chloride. The mixture is stirred at 4.5 hours and then concentrated under reduced pressure. The residue is repeatedly triturated with 10% (by volume) ethanol in methylene chloride. The ethanol-methylene chloride extracts are combined, filtered, the solvent removed and the residue dissolved in 50 ml. of the same ethanol-methylene chloride solvent mixture. The solution is chromatographed on a 180 g. silica gel column which is eluted with the same solvent mixture. After a forerun of 200 ml., eluate is collected in 11 ml. fractions. Fractions 23 through 70 are pooled and concentrated to give 0.998 g. of residue. This material is recrystallized from a mixture of 25 ml. each of acetone and hexane to give 783 mg. of material melting at 160°–162.5° (dec.).

Analysis: Calc'd. for $C_{17}H_{19}ClN_4O_8$ C, 46.11; H, 4.33; Cl, 8.01; N, 12.65. Found: C, 46.27; H, 4.48; Cl, 7.97; N, 12.61.

EXAMPLE 4

3'-(N²,N²-Dimethyloxamido)-oxanilic acid hemihydrate a. Ethyl 3'-nitro-oxanilate A solution that contains 39.5 gm. (0.286 mole) of m-nitroaniline, 50 ml. of dimethylformamide, 250 ml. of ethyl acetate and 36.52 gm. (0.358 mole) of triethylamine is cooled to 0° in an ice-bath. To the solution is added, slowly, 49.0 gm. (0.358 mole) of ethyl oxalyl chloride and the mixture is stirred in an ice-bath for one hour. The reaction mixture is warmed to room temperature overnight.

The precipitate is removed by filtration. The filtrate is evaporated to a semi-solid residue. The precipitate is partially dissolved in water and extracted with ethyl acetate. The organic phase is dried over magnesium sulfate. The drying agent is removed by filtration and the filtrate evaporated to dryness in vacuo. The residues are combined and recrystallized from ethanol to yield 43.5 gm. (64%) of yellow needles that melt at 148°–149°.

Analysis: Calc'd. for $C_{10}H_{10}N_2O_5$ C, 50.42; H, 4.23; N, 11.76. Found: C, 50.44; H, 4.28; N, 11.72.

b. N,N-Dimethyl-N'-(m-nitrophenyl)oxamide

A solution of 11.91 gm. (0.05 mole) of ethyl 3-nitro-oxanilate in 500 ml. of methylene chloride is cooled to 5° in an ice bath. There is added slowly, 25 ml. of dimethylamine and the mixture stirred for two hours in an ice-bath. The ice-bath is removed and the mixture allowed to stand at room temperature overnight.

The solution is evaporated to dryness in vacuo. The residue is recrystallized from ethanol. There is obtained 11.04 gm. (99%) of colorless needles that melt at 160°–161°.

Analysis: Calc'd. for $C_{10}H_{11}N_3O_4$ C, 50.63; H, 4.67; N, 17.72. Found: C, 50.63; H, 4.56; N, 17.69.

c. Ethyl 3'-(N²,N²-dimethyloxamido)oxanilate

A solution of 10.19 gm. (0.045 mole) of N,N-dimethyl-N'-(m-nitrophenyl)oxamide in 150 ml. of dioxane is placed in a hydrogenation bottle. To the solution is added 1 gm. of 10% palladium on carbon catalyst suspended in ethanol. The reaction mixture is hydrogenated at 3 atmospheres. The catalyst is removed by filtration and the filtrate evaporated to dryness in vacuo.

The oily residue is dissolved in 250 ml. of dry ethyl acetate. To the solution is added 5.46 gm. (0.054 mole) of triethylamine and the mixture cooled to 0° in an ice-bath. To the stirred solution is added 7.37 gm. (0.054 mole) of ethyl oxalyl chloride and the mixture is stirred in an ice-bath for one hour. The ice-bath is removed and the mixture is allowed to stand at room temperature overnight.

The precipitate is removed by filtration. The precipitate is washed several times with water. The insoluble material is recrystallized from ethanol-water. There is obtained 7.54 gm. of white crystalline material that melts at 175°–176°.

Analysis: Calc'd. for $C_{14}H_{17}N_3O_5$ C, 54.72; H, 5.58; N, 13.67. Found: C, 54.49; H, 5.69; N, 13.59.

d. 3'-(N²,N²-Dimethyloxamido)oxanilic acid hemihydrate

36 Ml. of 1 N sodium hydroxide is diluted to 100 ml. with water and 5.15 gm. (0.016 mole) of ethyl 3'-(N²,N²-dimethyloxamido)oxanilate added. The solution is stirred for twenty minutes at room temperature. The solution is cooled in an ice-bath and acidified with dilute hydrochloric acid. The precipitate is removed by filtration and washed several times with water. There is obtained 4.23 g. (91%) of a white solid material that melts at 228° (dec.).

Analysis: Calc'd. for $C_{12}H_{13}N_3O_5 \cdot 1/2\ H_2O$ C, 50.00; H, 4.89; N, 14.57. Found: C, 50.13; H, 4.70; N, 14.81.

EXAMPLE 5

Ethyl 3'-(N²-propyloxamido)oxanilate a. N-(m-nitrophenyl)-N'-propyl oxamide

To a stirred solution of 11.91 gm. (0.05 mole) of ethyl 3'-nitro-oxanilate in 500 ml. of methylene chloride is added 33 ml. of n-propylamine. The solution is allowed to stand at room temperature overnight. The solution is evaporated to dryness in vacuo. The residue is recrystallized from ethanol. There is obtained 11.65 gm. (93%) of short white needles that melt at 149°–150°.

Analysis: Calc'd. for $C_{11}H_{13}N_3O_4$ C, 52.58; H, 5.21; N, 16.72. Found: C, 52.47; H, 5.34; N, 16.61.

b. N-(m-aminophenyl-N'-propyl-oxamide

To a solution of 10.43 gm. (0.04 mole) of N-(m-nitrophenyl)-N'-propyl-oxamide in 150 ml. of dioxane is added 1 gm. of 10% palladium on carbon. The reaction mixture is hydrogenated under 3 atmospheres of hydrogen. The catalyst is removed by filtration. The filtrate is evaporated to dryness in vacuo. The residue is recrystallized from ethanol. There is obtained 7.71 gm. (87%) of colorless needles that melt at 126°–127°.

Analysis: Calc'd. for $C_{11}H_{15}N_3O_2$ C, 59.71; H, 6.83; N, 18.99. Found: C, 59.89; H, 6.73; N, 18.44.

c. Ethyl 3'-(N²-propyloxamido)oxanilate

A solution of 7.19 gm. (0.0325 mole) of N-(m-aminophenyl)-N'-propyl-oxamide in 250 ml. of ethyl acetate is stirred and there is added 3.95 gm. (0.039 mole) of triethylamine. The solution is cooled to 0° in an ice-bath. To the stirred solution is added 5.32 gm. (0.039 mole) of ethyl oxalyl chloride. The ice-bath is removed and the mixture allowed to stand at room temperature overnight.

The precipitate is removed by filtration. The precipitate is boiled with water and filtered. The insoluble residue is recrystallized from 95% ethanol. There is obtained 8.30 gm. (80%) of white needles that melt at 185°–186°.

Analysis: Calc'd. for $C_{15}H_{19}N_3O_5$ C, 56.06; H, 5.95; N, 13.08. Found: C, 56.05; H, 6.11; N, 13.26.

EXAMPLE 6

3,5-Bis-(N²-butyloxamido)-benzoic acid

A mixture of diethyl N,N'-[5-carboxy-1,3-phenylene]-dioxamate (1.0 gm.; 0.0029 mole), n-butyl amine (3.0 gm.) and methanol (50 ml.) is heated at reflux 0.5 hours. The reaction mixture is stirred at room temperature for eighteen hours. The reaction mixture is poured into water and the pH adjusted to pH=3 with 1.0 N HCl. The resulting solid is collected by filtration (1.0 gm.).

The crude product appears to be contaminated by some of the corresponding amine salt. This impurity is removed by dissolving the product in dimethyl sulfoxide and acidifying with 1.0 N HCl. The upgraded solid product is collected by filtration.

Analysis: Calc'd. for $C_{19}H_{24}N_4O_6$ C, 56.14; H, 6.45; N, 13.62. Found: C, 55.92; H, 6.19; N, 13.87.

nmr (DMSO-d): 10.9δ (s, broad, 2H, phenylHN), 9.0δ (t, broad, 2H, butyl NM, J 6Hz), 8.55δ (t, broad, 1H, aromatic H, $J_{meta}$=2Hz), 8.3δ (d, 2H, aromatic H, $J_{meta}$=2Hz), 3.2δ (q, broad 2H, N—CH$_2$—), 0.6–1.8δ (complex multiplet, 14H, (CH$_2$)$_2$CH$_3$).

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula I. The preferred method of administration is by inhalation into the lung by means of an aerosol liquid or powder for insufflation.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 gm.

The preferred compositions are those adapted for inhalation into the lung and containing a compound of the invention which is water-soluble. For treatment of allergic conditions of the nose, such as rhinitis, compositions adapted for contact with nasal linings are preferred.

Compositions for inhalation are of three basic types: (1) a powder mixture preferably micropulverized with particle size preferably from about 1 to about 5 microns; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be nontoxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.1 to about 10 mg. of compound in a single dose, administered parenterally or by inhalation in the compositions of this invention, are effective for preventing allergy attacks. More specifically, the single dose is from about 0.5 to about 5 mg. of compound. The oral and rectal dose is from about 1 to about 25 mg. in a single dose. More specifically, the single dose is from about 2 to about 20 mg. of compound. The dosage to be administered can be repeated up to four times daily. However, when it is necessary to repeat treatment, a preferred dosage schedule reduces the secondary treatment dosage of from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual insufflates 50 mg. of the ethyl 3'-(N$^2$-propyloxamido)oxanilate.

Four hours later the individual insufflates 0.2 mg. of the same compound and every four to six hours thereafter insufflates 0.2 mg. of the same compound until effective asthma prophylaxis is not provided. The individual then insufflates 50 mg. of the same compound, then reduces the insufflation dosage to 0.2 mg. four to six hours later. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise induced asthma, stress induced asthma, systemic anaphylaxis, and bird fancier's disease.

EXAMPLE 7

A lot of 10,000 tablets, each containing 5 mg. of ethyl 3'-chloro-5'-cyano-3'-[N$^2$-[2-hydroxy-1,1-bis(-hydroxymethyl)ethyl]oxamido]oxanilate is prepared from the following types and amounts of ingredients:

| | |
|---|---|
| Ethyl 3'-chloro-5'-cyano-3'-[N$^2$-[2-hydroxy-1,1-bis-(hydroxymethyl)ethyl]oxamido]-oxanilate | 50 gm. |
| Dicalcium phosphate | 1,000 gm. |
| Methylcellulose, U.S.P. (15 cps) | 60 gm. |
| Talc | 150 gm. |
| Corn starch | 200 gm. |
| Magnesium stearate | 10 gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of one tablet every four to six hours.

EXAMPLE 8

One thousand two-piece hard gelatin capsules, each containing 10 mg. of ethyl 3'-(N$^2$-propyloxamido)oxanilate are prepared from the following types and amounts of ingredients:

| | |
|---|---|
| Ethyl 3'-(N$^2$-propyloxamido)-oxanilate | 10 gm. |
| Talc | 150 gm. |
| Magnesium stearate | 1 gm. |

The ingredients are mixed well and filled into capsules of the proper size.

Capsules so prepared are useful in preventing attacks of bronchial asthma at a dose of one capsule every four to six hours.

EXAMPLE 9

One thousand tablets, each containing 10 mg. of N,N''-[2-chloro-5-cyano-m-phenylene]bis-[N'-(2-hydroxy)-1,1-bis(hydroxymethyl)ethyl]oxamide are prepared from the following types and amounts of ingredients:

| | |
|---|---|
| N',N''-[2-chloro-5-cyano-m-phenylene]bis-[N'-(2-hydroxy)-1,1-bis(hydroxymethyl)ethyl]-oxamide | 10 gm. |
| Microcrystalline cellulose NF | 410 gm. |
| Starch | 100 gm. |
| Magnesium stearate powder | 3 gm. |

The ingredients are screened and blended together and pressed into tablets.

The tablets are useful to protect against food allergy at a dose of one tablet before meals.

EXAMPLE 10

One thousand tablets, each containing 10 mg. of ethyl 2'-chloro-5'-cyano-3'-[N$^2$-[2-hydroxy-1,1-bis(-hydroxymethyl)ethyl]oxamido]oxanilate are prepared from the following types and amounts of ingredients:

| | |
|---|---|
| Ethyl 2'-chloro-5'-cyano-3'-[N$^2$-[2-hydroxy-1,1-bis-(hydroxymethyl)ethyl]-oxamido]-oxanilate | 10 gm. |
| Microcrystalline cellulose NF | 410 gm. |

| | |
|---|---|
| Starch | 100 gm. |
| Magnesium stearate powder | 3 gm. |

The ingredients are screened and blended together and pressed into tablets.

The tablets are useful to protect against food allergy at a dose of one tablet before meals.

EXAMPLE 11

A sterile preparation suitable for intramuscular injection and containing 10 mg. of ethyl 3'-(N$^2$-propyloxamido)-oxanilate in each milliliter is prepared from the following ingredients:

| | |
|---|---|
| Ethyl 3'-(N-propyloxamido)-oxanilate | 10 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected for prophylactic treatment of allergic rhinitis.

EXAMPLE 12

Six hundred ml. of an aqueous solution containing 5 mg. of the sodium 3'-(N$^2$,N$^2$-dimethyloxamido)-oxanilate per ml. is prepared as follows:

| | |
|---|---|
| Sodium 3'-(N$^2$,N$^2$-dimethyl-oxamido)-oxanilate | 3 gm. |
| Sodium chloride | 5 gm. |
| Water for injection q.s. | 600 ml. |

The compound and sodium chloride are dissolved in sufficient water to make 600 ml. and sterile filtered.

The solution is placed in nebulizers designed to deliver 1 ml. of solution per spray.

The solution is inhaled into the lungs every four to six hours for prevention of asthmatic attacks.

EXAMPLE 13

A powder mixture consisting of 0.5 gram of sodium 3'-(N$^2$-propyloxamido)-oxanilate and sufficient lactose to make 50 grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 14

A powder mixture consisting of 0.5 gram of N',N''-[2-chloro-5-cyano-m-phenylene]bis-[N'-(2-hydroxy)-1,-1-bis-(hydroxymethyl)ethyl]oxamide and sufficient lactose to make 5 grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 15

12.5 Grams of an aerosol composition are prepared from the following ingredients:

| | |
|---|---|
| Sodium 2'-chloro-5'-cyano-2'-[N$^2$-[2-hydroxy-1,1-bis-(hydroxymethyl)ethyl]-oxamido]oxanilate | .525 gm. |
| Freon 12 | 1.440 gm. |
| Freon 114 | 2.160 gm. |
| Water | 7.775 gm. |
| Sorbitan monoleate | 0.600 gm. |

The compound is dissolved in the water and chilled to −30° C. and added to the chilled Freons. The 12.5 grams of compositions are added to a 13 cc. plastic coated bottle and capped with a metering valve. The metering valve releases 80 mg. of composition in an aerosol. The aerosol is inhaled every four to six hours for prevention of asthmatic attacks.

EXAMPLE 16

In individuals who require continual treatment in the Examples 7 through 15, the dosage of the Example is given initially and each succeeding administration of the drug is at 1/20–1/50 of the initial dosage. This maintenance dosing is continued until effective allergy prophylaxis is not obtained. The initial dosage of Examples 7 through 15 is then started once more, followed by the maintenance dosages.

EXAMPLE 17

After allowing for the differing solubilities of the compounds and the activity of the particular compound as measured, for example, by the in vivo rat passive cutaneous anaphylaxis assay, a suitable quantity of each of the compounds of Tables I through III and Examples 1 through 6 is substituted for the active compound in the compositions and uses of Examples 7 through 16. Results showing anti-allergy activity are obtained.

EXAMPLE 18

The rat passive cutaneous anaphylaxis assay is executed in the following manner:

Female Sprague-Dawley 250 gm. rats are skin-sensitized with rat anti-ovalbumin homocytotropic antibody that is heat labile and has a passive cutaneous anaphylaxis titer of 1:128. After a 72-hour latency period, the animals are challenged i.v. with 4 mg. ovalbumin (OA) + 5 mg. Evans blue dye and the test compound. Where the test compound is insufficiently soluble in an appropriate vehicle to be administered i.v., the compound is administered orally from five to sixty minutes prior to antigen challenge. Thirty minutes later the extravascular bluing that results from antigen antibody combination at the skin site is used. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

Following the above procedure, ethyl 2'-chloro-5'-cyano-3'-[N²-[2-hydroxy-1,1-bis(hydroxymethyl)ethyl]oxamido]oxanilate is tested in the rat passive cutaneous assay by the oral route. The inhibitory dose$_{50}$ for this compound is 5 mg./kg.

We claim:

1. Compounds of the formula:

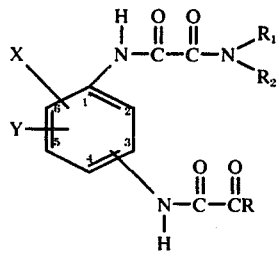

wherein X and Y are the same or different and are selected from the group consisting of hydrogen, fluorine, chlorine, bromine, trifluoromethyl, acetyl, phenyl, alkyl of one to six carbon atoms, inclusive, alkoxy of one to six carbon atoms, inclusive, and nitro;

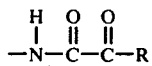

is at the 3 or 4 position; $R_1$ and $R_2$ are the same or different and are selected from the group consisting of hydrogen, alkyl of one to six carbon atoms, inclusive, monohydroxyalkyl wherein alkyl is from two to six carbon atoms, inclusive, and the hydroxy is not on the alpha carbon atom, and tris(hydroxymethyl)methyl with the proviso that when $R_1$ has a tertiary carbon atom adjacent to the nitrogen atom, then $R_2$ does not have a tertiary carbon atom adjacent to the nitrogen atom; R is OM wherein M is selected from the group consisting of hydrogen, a physiologically acceptable metal or amine cation, and alkyl of one to six carbon atoms, inclusive.

2. Compounds in accordance with claim 1 wherein X and Y are the same or different and are selected from the group consisting of hydrogen, fluorine, chlorine, trifluoromethyl, acetyl, phenyl, alkyl of one to four carbon atoms, inclusive, alkoxy of one to four carbon atoms, inclusive, and nitro; $R_1$ and $R_2$ are the same or different and are selected from the group consisting of hydrogen, alkyl of one to four carbon atoms, inclusive, monohydroxyalkyl wherein alkyl is from two to four carbon atoms, inclusive, and the hydroxy is not on the alpha carbon atom, and tris(hydroxymethyl)methyl with the proviso that when $R_1$ has a tertiary carbon atom adjacent to the nitrogen atom, then $R_2$ does not have a tertiary carbon atom adjacent to the nitrogen atom; R is OM wherein M is selected from the group consisting of hydrogen, a physiologically acceptable metal or amine cation, and alkyl of one to four carbon atoms, inclusive.

3. Compounds according to claim 1 wherein X and Y are the same or different and are selected from the group consisting of hydrogen, fluorine, chlorine, trifluoromethyl, acetyl, phenyl, alkyl of one to three carbon atoms, inclusive, alkoxy of one to three carbon atoms, inclusive, and nitro;

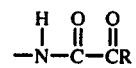

is at the 3 position; $R_1$ and $R_2$ are the same or different and are selected from the group consisting of hydrogen, alkyl of one to three carbon atoms, inclusive, monohydroxyalkyl wherein alkyl is two or three carbon atoms, inclusive, and hydroxy is not on the alpha carbon atom; R is OM wherein M is selected from the group consisting of hydrogen, a physiologically acceptable metal or amine cation and alkyl of one to three carbon atoms, inclusive.

4. Compounds according to claim 1 wherein X and Y are the same or different, are located at the 2 and 5 positions and are selected from the group consisting of hydrogen, fluorine, chlorine, trifluoromethyl, alkyl of one to three carbon atoms, inclusive, and alkoxy of one to three carbon atoms, inclusive;

is at the 3 position; R is OM wherein M is selected from the group consisting of hydrogen and a physiologically acceptable metal or amine cation.

5. 3'-(N²,N²-Dimethyloxamido)oxanilic acid hemihydrate according to claim 1.

6. Ethyl 3'-(N²-propyloxamido)oxanilate according to claim 1.

7. Ethyl 3'-(N²,N²-dimethyloxamido)oxanilate according to claim 1.

8. A compound in accordance with claim 1 wherein X and Y are hydrogen, $R_1$ and $R_2$ are methyl and R is OM.

9. A pharmaceutical composition which comprises a compound of the formula:

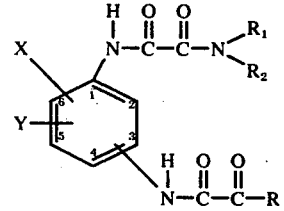

wherein X and Y are the same or different and are selected from the group consisting of hydrogen, fluorine, chlorine, bromine, trifluoromethyl, acetyl, phenyl, alkyl of one to six carbon atoms, inclusive, alkoxy of one to six carbon atoms, inclusive, and nitro;

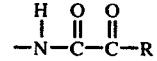

is at the 3 or 4 position; $R_1$ and $R_2$ are the same or different and are selected from the group consisting of hydrogen, alkyl of one to six carbon atoms, inclusive, monohydroxyalkyl wherein alkyl is from two to six carbon atoms, inclusive, and the hydroxy is not on the alpha carbon atom and tris(hydroxymethyl)methyl with the proviso that when $R_1$ has a tertiary carbon atom adjacent to the nitrogen atom, then $R_2$ does not have a tertiary carbon atom adjacent to the nitrogen atom; R is OM wherein M is selected from the group consisting of hydrogen, a physiologically acceptable metal or amine cation, and alkyl of one to six carbon atoms, inclusive; in association with a pharmaceutical carrier.

10. A composition in accordance with claim 9 wherein the compound is ethyl 3'-($N^2,N^2$-dimethyloxamido)oxanilate.

11. A method for the prophylactic treatment of allergy of a reagin or non-reagin mediated nature which comprises administering to a mammal in need of said treatment an anti-allergy effective amount of a compound of the formula

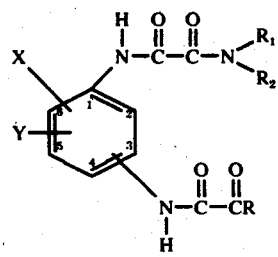

wherein X and Y are the same or different and are selected from the group consisting of hydrogen, fluorine, chlorine, bromine, trifluroromethyl, acetyl, phenyl, alkyl of one to six carbon atoms, inclusive, alkoxy of one to six carbon atoms, inclusive, and nitro;

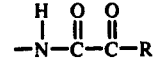

is at the 3 of 4 position; $R_1$ and $R_2$ are the same or different and are selected from the group consisting of hydrogen, alkyl of one to six carbon atoms, inclusive, monohydroxyalkyl wherein alkyl is from two to six carbon atoms, inclusive, and the hydroxy is not on the alpha carbon atom, and tris(hydroxymethyl)methyl with the proviso that when $R_1$ has a tertiary carbon atom adjacent to the nitrogen atom, the $R_2$ does not have a tertiary carbon atom adjacent to the nitrogen atom; R is OM wherein M is selected from the group consisting of hydrogen, a physiologically acceptable metal or amine cation, and alkyl of one to six carbon atoms, inclusive.

12. A method in accordance with claim 11 wherein the compound is ethyl 3'-($N^2,N^2$-dimethyloxamido)oxanilate.

* * * * *